(12) United States Patent
Ma et al.

(10) Patent No.: US 12,188,918 B1
(45) Date of Patent: Jan. 7, 2025

(54) INTELLIGENT MONITORING METHOD FOR SOIL MOISTURE STATUS BASED ON REMOTE SENSING TECHNOLOGY

(71) Applicant: INSTITUTE OF FARMLAND IRRIGATION OF CAAS, Henan (CN)

(72) Inventors: Chunya Ma, Henan (CN); Fuyi Duan, Henan (CN); Yongshen Fan, Henan (CN); Yun Gao, Henan (CN); Zhen Chen, Henan (CN); Peng Li, Henan (CN); Xiulu Sun, Henan (CN); Hua Cao, Henan (CN); Wei Zhan, Henan (CN); Yinbo Cao, Henan (CN); Wanna Fu, Henan (CN)

(73) Assignee: INSTITUTE OF FARMLAND IRRIGATION OF CAAS, Xinxiang (CN)

( * ) Notice: Subject to any disclaimer, the term of this patent is extended or adjusted under 35 U.S.C. 154(b) by 0 days.

(21) Appl. No.: 18/774,856

(22) Filed: Jul. 16, 2024

Related U.S. Application Data

(63) Continuation of application No. PCT/CN2024/103242, filed on Jul. 3, 2024.

(30) Foreign Application Priority Data

Oct. 9, 2023 (CN) .......................... 202311293604.5

(51) Int. Cl.
*G01N 33/24* (2006.01)
*G01N 21/17* (2006.01)

(52) U.S. Cl.
CPC .......... *G01N 33/246* (2013.01); *G01N 21/17* (2013.01); *G01N 2021/1765* (2013.01);
(Continued)

(58) Field of Classification Search
None
See application file for complete search history.

(56) References Cited

U.S. PATENT DOCUMENTS

| 10,584,964 B2 * | 3/2020 | Kasahara | G01C 9/02 |
| 11,041,841 B2 * | 6/2021 | Niemann | G01N 33/246 |
| 2024/0087311 A1 * | 3/2024 | Soldevilla-Martinez | G06V 20/188 |

FOREIGN PATENT DOCUMENTS

| CN | 106525753 A | * | 3/2017 | |
| CN | 108717044 A | * | 10/2018 | G01N 21/17 |

(Continued)

*Primary Examiner* — Peter J Macchiarolo
*Assistant Examiner* — Jermaine L Jenkins

(57) ABSTRACT

Disclosed is an intelligent monitoring method for soil moisture status based on remote sensing technology, including the following steps: dividing a monitoring region into a plurality of sub-regions by a processing end, acquiring image data of various sub-regions on the basis of remote sensing satellites, acquiring multi-source data related to soil moisture status of the monitoring region on the basis of sensor devices, and pre-processing the image data and the multi-source data; comprehensively analyzing the image data and the multi-source data, and assessing soil moisture status of the various sub-regions; and comprehensively analyzing overall soil moisture status of the monitoring region according to the soil moisture status of the various sub-regions. The soil moisture status of the monitoring region is assessed after the multi-source data is comprehensively analyzed by the monitoring method, bringing about a more comprehensive and accurate analysis.

6 Claims, 1 Drawing Sheet

S1: divide a monitoring region into a plurality of sub-regions by a processing end, acquire image data of various sub-regions on the basis of remote sensing satellites, acquire multi-source data related to soil moisture status from the monitoring region on the basis of sensor devices, and pre-process the image data and the multi-source data S2: comprehensively analyze the image data and the multi-source data, and assess soil moisture status of the various sub-regions S3: comprehensively analyze overall soil moisture status of the monitoring region according to the soil moisture status of the various sub-regions S4: present the overall soil moisture status of the monitoring region in a visualization manner S5: send a visualization report to an administrator

(52) U.S. Cl.
CPC .................. *G01N 2021/178* (2013.01); *G01N 2021/1797* (2013.01); *G01N 2201/0407* (2013.01)

(56) References Cited

FOREIGN PATENT DOCUMENTS

| | | | | |
|---|---|---|---|---|
| CN | 109187417 A | * | 1/2019 | ............. G01N 21/25 |
| CN | 107389895 B | * | 8/2019 | ........... G01N 33/246 |
| CN | 110907367 A | * | 3/2020 | ............. G01N 1/286 |
| CN | 116737729 A | | 9/2023 | |

* cited by examiner

S1: divide a monitoring region into a plurality of sub-regions by a processing end, acquire image data of various sub-regions on the basis of remote sensing satellites, acquire multi-source data related to soil moisture status from the monitoring region on the basis of sensor devices, and pre-process the image data and the multi-source data

S2: comprehensively analyze the image data and the multi-source data, and assess soil moisture status of the various sub-regions

S3: comprehensively analyze overall soil moisture status of the monitoring region according to the soil moisture status of the various sub-regions

S4: present the overall soil moisture status of the monitoring region in a visualization manner

S5: send a visualization report to an administrator

INTELLIGENT MONITORING METHOD FOR SOIL MOISTURE STATUS BASED ON REMOTE SENSING TECHNOLOGY

CROSS-REFERENCE TO RELATED APPLICATIONS

This application is a continuation of PCT/CN2024/103242, filed Jul. 3, 2024 and claims priority of Chinese Patent Application No. 202311293604.5, filed on Oct. 9, 2023, the entire contents of which are incorporated herein by reference.

TECHNICAL FIELD

The present disclosure relates to the technical field of soil monitoring, and specifically relates to an intelligent monitoring method for soil moisture status based on remote sensing technology.

BACKGROUND

Soil moisture status, as one of the key parameters for measuring humidity and moisture content of soil, is of great significance in the fields of agriculture, water resource management, and environmental protection, etc. Suitable soil moisture status helps decision makers to better carry out farmland irrigation, drought monitoring, flood prevention and management, etc.

An intelligent monitoring system for soil moisture status based on remote sensing technology utilizes a combination of remote sensing technology, sensor technology and data analysis technology, aiming at real-time monitoring and assessment of soil moisture status that refers to the moisture content and humidity of soil.

The prior art has the following deficiencies:

In the existing monitoring systems, the overall soil moisture status of a monitoring region is typically determined by acquiring image data of the monitoring region by means of remote sensing satellites, preforming color segmentation of soil on the basis of the image data, and comparing color grids that represent good soil moisture status with color grids that represent poor soil moisture status. However, when there are influence factors (such as rainy or heavy fog weather), the accuracy of this analysis can be affected, thus affecting the administrator's determination.

Therefore, the present application provides an intelligent monitoring method for soil moisture status based on remote sensing technology to assess the soil moisture status of the monitoring region after comprehensively analyzing multi-source parameters, bringing about a higher accuracy.

SUMMARY

An objective of the present disclosure is to provide an intelligent monitoring method for soil moisture status based on remote sensing technology to overcome the deficiencies in the above background.

To realize the above objective, the present disclosure provides the following technical solutions: an intelligent monitoring method for soil moisture status based on remote sensing technology includes the following steps:

S1: dividing a monitoring region into a plurality of sub-regions by a processing end, acquiring image data of various sub-regions on the basis of remote sensing satellites, acquiring multi-source data related to soil moisture status of the monitoring region on the basis of sensor devices, and pre-processing the image data and the multi-source data;

S2: comprehensively analyzing the image data and the multi-source data, and assessing soil moisture status of the various sub-regions;

S3: comprehensively analyzing overall soil moisture status of the monitoring region according to the soil moisture status of the various sub-regions;

S4: presenting the overall soil moisture status of the monitoring region in a visualization manner; and S5: sending a visualization report to an administrator.

Preferably, in step S2, the image data and the multi-source data are comprehensively analyzed, the image data including a color segmentation index, and the multi-source data including a humidity coefficient and a moisture content float coefficient.

Preferably, in step 2, the assessing soil moisture status of the various sub-regions includes the following steps:

S2. 1: calculating a moisture status coefficient by combining the color segmentation index, the humidity coefficient, and the moisture content float coefficient through the following expression:

$$sq_x = \frac{\alpha * sd_x^2 + 1}{\ln\sqrt{\beta * ys_f + \gamma * hs_f}}$$

where $sd_x$ represents the humidity coefficient, $ys_f$ represents the color segmentation index, $hs_f$ represents the moisture content float coefficient, and $\alpha$, $\beta$, and $\gamma$ represent proportionality coefficients of the humidity coefficient, the color segmentation index, and the moisture content float coefficient, respectively, $\alpha$, $\beta$, and $\gamma$ being greater than 0; and S2. 2: assessing soil moisture status in a sub-region to be good if a value of the moisture status coefficient $sq_x$ is greater than or equal to a moisture status threshold, and assessing soil moisture status in a sub-region to be poor if a value of the moisture status coefficient $sq_x$ is less than the moisture status threshold.

Preferably, in step S3, the comprehensively analyzing overall soil moisture status of the monitoring region according to the soil moisture status of the various sub-regions includes the following steps:

S3. 1: acquiring the number of sub-regions, and acquiring values of the moisture status coefficient $sq_x$ of the various sub-regions;

S3. 2: calculating an average moisture status coefficient value of all the sub-regions;

S3. 3: calculating a moisture status coefficient dispersion degree of the monitoring region on the basis of the values of the moisture status coefficient $sq_x$ and the average moisture status coefficient value of the sub-regions; and S3. 4: analyzing soil moisture status of the monitoring region and a variation trend of the soil moisture status according to the moisture status coefficient dispersion degree of the monitoring region.

Preferably, in step S3. 4, an expression for calculating the moisture status coefficient dispersion degree of the monitoring region is as follows:

$$jq_s = \sqrt{\frac{\sum_{b=1}^{c}(R_b - \overline{R})^2}{c-1}}$$

where b={1, 2, 3, ..., c}, c representing the number of sub-regions, and being a positive integer, $R_b$ represents a value of the moisture status coefficient $sq_x$ in a $b_{th}$ sub-region, and $\overline{R}$ represents the average moisture status coefficient value;

if the average moisture status coefficient value is greater than or equal to the moisture status threshold and the moisture status coefficient dispersion degree is less than or equal to a dispersion threshold, the overall soil moisture status of the monitoring region being analyzed to be good, and trending towards good in the future;

if the average moisture status coefficient value is greater than or equal to the moisture status threshold and the moisture status coefficient dispersion degree is greater than the dispersion threshold, the overall soil moisture status of the monitoring region being analyzed to be moderate, and unstable factors existing in the future development trend of the soil moisture status;

if the average moisture status coefficient value is less than the moisture status threshold and the moisture status coefficient dispersion degree is greater than the dispersion threshold, the overall soil moisture status of the monitoring region being analyzed to be poor, and unstable factors existing in the future development trend of the soil moisture status; and if the average moisture status coefficient value is less than the moisture status threshold and the moisture status coefficient dispersion degree is less than or equal to the dispersion threshold, the overall soil moisture status of the monitoring region being analyzed to be very poor, and trending towards bad in the future.

Preferably, an expression for calculating the color segmentation index is as follows:

$$ys_f = \frac{sc_t}{sh_t} + \frac{sc_b}{sh_b}$$

where $ys_f$ represents the color segmentation index, $sh_t$ represents the number of grids occupied by regions with good soil moisture status in soil exposed regions, $sc_t$ represents the number of grids occupied by regions with poor soil moisture status in the soil exposed regions, $sh_b$ represents the number of grids occupied by regions with good soil moisture status in vegetated regions, and $sc_b$ represents the number of grids occupied by regions with poor soil moisture status in the vegetated regions.

Preferably, an expression for calculating the humidity coefficient is as follows:

$$sd_x = \sum_{i=1}^{n} e^{a_i * sd_i}$$

where $sd_x$ represents the humidity coefficient, i={1, 2, ..., n}, n being a positive integer, and representing the number of monitoring points set at different soil depths in the sub-region, $sd_i$ represents soil humidity at an $i_{th}$ monitoring point, and $a_i$ represents a weight of the soil humidity at the $i_{th}$ monitoring point, $a_i$ being greater than 0.

Preferably, an expression for calculating the moisture content float coefficient is as follows:

$$hs_f = \int_{t_x}^{t_y} H(t)dt + \int_{t_i}^{t_j} H(t)dt$$

where H(t) represents real-time moisture content of soil in the sub-region, $[t_x, t_y]$ represents a period for early-warning of environmental evapotranspiration in the sub-region, and $[t_i, t_j]$ represents a period for early-warning of groundwater level in the sub-region.

Preferably, the logic for acquiring the period for early-warning of environmental evapotranspiration in the sub-region is as follows: calculating environmental evapotranspiration of the sub-region by means of an evaporation dish, a period in which evapotranspiration is greater than an evapotranspiration threshold being the period for early-warning of environmental evapotranspiration in the sub-region.

Preferably, the logic for acquiring the period for early-warning of groundwater level in the sub-region is as follows: acquiring groundwater level of the sub-region by means of a radar, a period in which the groundwater level is lower than a water level threshold being the period for early-warning of groundwater level in the sub-region.

In the above technical solutions, the present discourage provides the following technical effects and advantages.

In the present disclosure, the monitoring region is divided into a plurality of sub-regions by the processing end, and the sub-regions can be delineated in equal area, the image data of various sub-regions is acquired on the basis of the remote sensing satellites, the multi-source data related to the soil moisture status of the monitoring region is acquired on the basis of the sensor devices, and the image data and the multi-source data are pre-processed; and the image data and the multi-source data are comprehensively analyzed, and after the soil moisture status of various sub-regions is assessed, the overall soil moisture status of the monitoring region is comprehensively analyzed according to the soil moisture status of the various sub-regions. By means of this monitoring method, the soil moisture status of the monitoring region is assessed after the multi-source data is comprehensively analyzed, bringing about a more comprehensive and accurate analysis.

In the present disclosure, the moisture status coefficient is calculated by combining the color segmentation index, the humidity coefficient and the moisture content float coefficient, bringing about a more comprehensive and accurate analysis. Moreover, after the soil moisture status of a plurality of sub-regions is analyzed, the overall soil moisture status of the monitoring region as well as the development trend of the soil moisture status are determined according to the analyzed soil moisture status of the plurality of sub-regions, which is conducive to formulating a management policy by the administrator.

BRIEF DESCRIPTION OF THE DRAWINGS

For illustrating the technical solutions of the embodiments in the present application or in the prior art more clearly, the attached drawings required in the embodiments will be described briefly below. Obviously, the attached drawings described below are merely some embodiments recorded in the present disclosure. For those ordinary skilled in the art, other drawings can be obtained according to these drawings.

FIG. 1 is a flow chart of a method according to the present disclosure.

DETAILED DESCRIPTION

For clearer objective, technical solutions and advantages of the present disclosure, the technical solutions of the embodiments in the present disclosure will be described clearly and completely by reference to the attached drawings of the embodiments in the present disclosure below. Obviously, the embodiments described are only some, rather than all embodiments of the present disclosure. On the basis of the embodiments of the present disclosure, all other embodiments obtained by those ordinary skilled in the art without creative efforts are included in the scope of protection of the present disclosure.

Embodiment 1: as shown in FIG. 1, this embodiment provides an intelligent monitoring method for soil moisture status based on remote sensing technology, and the monitoring method includes the following steps.

A monitoring region is divided into a plurality of sub-regions by a processing end, the sub-regions can be delineated in equal area, and the following steps are included.

Determination of monitoring region: first, an entire region to be monitored is determined, which may be a farmland, a watershed, an ecosystem, or other geographic regions.

Selection of delineation factors: factors for delineation of sub-regions are determined; and generally, area is a common delineation factor, but other factors, such as land-use type, topography, precipitation distribution, etc., may also be considered.

Data preparation: data related to the selected delineation factors is collected or acquired, for example, if area is selected as a delineation factor, area data of each sub-region needs to be acquired.

Determination of delineation criteria: delineation criteria are determined according to the selected delineation factors and data, for example, if area is taken as a delineation factor, minimum and maximum area limits for each sub-region may be set, or delineation is performed according to a certain interval.

Delineation of sub-regions: a computer program or geographic information system (GIS) tool is used to divide the monitoring region into a plurality of sub-regions according to the delineation criteria; and the delineation process may be automated, and delineation is performed according to predetermined rules, or performed by manually drawing boundary lines.

Validation and optimization: it is verified whether the results of the delineation are as expected and as required for monitoring and analysis; and if necessary, the sub-regions may be adjusted and optimized to ensure that the delineation is reasonable and practical.

Identification and management of sub-regions: each sub-region is assigned with a unique identifier or code for identification and management during subsequent monitoring and data analysis.

Image data of various sub-regions is acquired on the basis of remote sensing satellites, and the following steps are included.

Satellite selection and orbit planning: according to the location and characteristics of the monitoring region, suitable remote sensing satellites are selected, and satellite orbits and observation times are planned to ensure that the satellite can capture images of the desired sub-region.

Selection of remote sensing data sources: suitable remote sensing data sources are selected, which may include public satellite data (such as Landsat, moderate-resolution imaging spectroradiometer (MODIS), and Sentinel) or commercial remote sensing data (such as WorldView, and QuickBird).

Data acquisition and download: remote sensing image data of the desired sub-region is acquired through a platform of a satellite data provider or a data archiving center; and it is ensured that the data selected match the monitoring region and time period.

Data pre-processing: some pre-processing, including decompression, atmospheric correction, radiometric calibration and other operations, is generally needed on the downloaded remote sensing data, to ensure the quality and consistency of the data.

Sub-region image cropping: according to the boundary information of the sub-region, a remote sensing image is cropped using GIS or image processing software to retain only the part of the image within the sub-region.

Data calibration: if a plurality of satellite images or sensor data are used at the same time, it is required to ensure that they are in the same coordinate and projection system for conveniently performing the subsequent data analysis.

Image stitching (alternative): if the sub-region spans a plurality of satellite images or dates of capture, image stitching may be required to produce a complete image of the sub-region.

Image quality assessment: quality assessment is performed on the image of the sub-region to check for cloud cover, shadows or other problems that may affect subsequent data analysis and monitoring.

Data storage and management: the processed image data of the sub-region is stored and managed to ensure data security and accessibility.

Periodic data acquisition (alternative): if regular monitoring of variations in the sub-region is required, an automated data acquisition program may be set up to acquire the latest remote sensing image data.

Multi-source data related to soil moisture status of the monitoring region is acquired on the basis of sensor devices, and the following steps are included.

Sensor selection: according to the need of monitoring and soil moisture status parameters, suitable sensor devices are selected; and these sensors may include soil humidity sensors, soil temperature sensors, precipitation sensors, and weather stations.

Location arrangement: the sensor devices are arranged in the monitoring region, and it is ensured that the location and arrangement of the sensors are representative of the soil conditions in the entire region; and factors such as soil type, topography, and vegetation cover needs to be taken into account in the arrangement density and the location selection of the sensors.

Sensor calibration: prior to being mounted, the sensors are calibrated to ensure the accuracy and consistency of data measured by the sensors; and the calibration usually involves comparison and adjustment using standard soil samples.

Data acquisition setting: data acquisition parameters of the sensor devices are set, including sampling frequency, data storage mode, transmission mode, etc., to ensure that the sensors are able to collect soil moisture status data as needed.

Sensor data acquisition: the sensor devices are activated for data acquisition; and the sensors will regularly measure soil moisture status parameters and store the data in the devices or send the same to a data center or cloud via wireless transmission.

Data quality control: the quality of sensor data is regularly checked to ensure that there is no drift or anomalies in the data; and data correction and repair are performed as needed.

Data integration: the soil moisture status data obtained by the sensors is integrated with other related data sources (such as meteorological data, and remote sensing data) to obtain more comprehensive information; and temporal and spatial consistency of the data is ensured.

Data storage and management: a data storage and management system is established to ensure secure storage and easy access to the sensor data; and the data is backed up to prevent data from losing.

The consistency and quality of the data are ensured after the image data and the multi-source data are pre-processed, and the following steps are included.

Data cleansing: first, the data is cleansed to remove all obvious outliers, errors, or missing data, which may be done by writing a script or using data processing software.

Correction: data calibration is performed; radiometric correction, atmospheric correction, geometric correction, etc., are performed according to data type and sensor characteristics, to ensure data accuracy and comparability; and the specific correction method depends on the data type and the sensor.

Data registration: if a plurality of data sources are used, it is required to make sure that the data is under the same coordinate system, so that the data can be properly overlaid and compared, which may require image registration or geographic coordinate conversion.

Cloud and shadow processing: cloud cover and shadows on the remote sensing image are detected and masked, to minimize their impact on data quality, which typically requires cloud detection algorithms and image processing techniques.

Denoising: for the sensor data, appropriate denoising techniques, including the use of filters or signal processing methods to smooth the data, are used to reduce the impact of noise on the data.

Data interpolation: if there are missing data points, interpolation methods may be used to estimate the values of these points; and linear interpolation, kriging interpolation, and other methods may be used to fill in missing data.

Data normalization: data from different data sources is normalized to ensure that they have the same scale and scope for convenient comparison and integration.

Outlier detection and processing: outliers in the data are detected and processed; and those outliers may result from sensor fault or other causes, and may be identified and processed by statistical methods.

Time synchronization: if time-series data is processed, it is required to ensure that timestamps of different data sources are synchronized, so that the data can be properly analyzed and compared.

The image data and the multi-source data are comprehensively analyzed, and the soil moisture status of various sub-regions is assessed, and overall soil moisture status of the monitoring region is comprehensively analyzed according to the soil moisture status of the various sub-regions.

The overall soil moisture status of the monitoring region is presented in a visualization manner, such as making a moisture status map, chart, or report, which helps a user to better understand spatial distribution and variation trend of soil moisture status, the report is sent to an administrator, and the following steps are included.

Selection of visualization tools: according to the needs of the analysis and user preferences, appropriate visualization tools, such as maps, charts or reports, are selected.

Creation of moisture status map: if the creation of a moisture status map is selected, GIS software or an online mapping platform may be used to create the map; and color-coding or symbols are used on the map to indicate the level of soil moisture status in different sub-regions, so that the user can understand the spatial distribution at a glance.

Chart creation: if the chart creation is selected, line charts, histogram, or thermodynamic diagrams may be created to present trends and variations of the soil moisture status data; and data from different sub-regions or time points can be compared in the chart.

Report generation: if a report needs to be generated, the results of visualization and the analysis results are integrated into the report; and key soil moisture status data, trend analysis, key observations, and recommendations are to be included in the report.

Report design: the layout and style of the report are designed to ensure that the report is easy to read and understand, which may include graph, tables, headings and explanatory text.

Report delivery: the generated report is sent to the administrator or relevant stakeholders via email, online sharing platforms, or hard copy reports.

Regular update: if soil moisture status monitoring is a regularly conducted activity, it is ensured that report is updated regularly to reflect the latest data and trends.

User training (alternative): if necessary, the administrator or other users are provided with training to ensure that they can properly understand and use the information in the report.

In the present application, the monitoring region is divided into a plurality of sub-regions by the processing end, and the sub-regions are delineated in equal area, the image data of various sub-regions is acquired on the basis of the remote sensing satellites, the multi-source data related to the soil moisture status in the monitoring region is required on the basis of the sensor devices, and the image data and the multi-source data are pre-processed; and the image data and the multi-source data are comprehensively analyzed, and after the soil moisture status of various sub-regions is assessed, the overall soil moisture status of the monitoring region is comprehensively analyzed according to the soil moisture status of the various sub-regions. By means of this monitoring method, the soil moisture status of the monitoring region is assessed after the multi-source data is comprehensively analyzed, bringing about a more comprehensive and accurate analysis.

Embodiment 2: the image data and the multi-source data are comprehensively analyzed, and after the soil moisture status of various sub-regions is assessed, the overall soil moisture status of the monitoring region is comprehensively analyzed according to the soil moisture status of the various sub-regions.

The image data includes a color segmentation index, and the multi-source data includes a humidity coefficient and a moisture content float coefficient.

The logic for acquiring the color segmentation index is as follows.

Images of the sub-regions are taken by remote sensing satellites, and boundaries of the sub-regions in the images are determined after the images are scaled in equal proportions.

The images are subjected to first segmentation on the basis of the color segmentation technique to segment soil exposed regions and vegetated regions in the images; and the images are subjected to second segmentation on the basis of the color segmentation technique to segment regions with good soil moisture status and regions with poor soil moisture status in the soil exposed regions, and to segment regions with good soil moisture status and regions with poor soil moisture status in the vegetated regions.

Generally speaking, in one monitoring region, a color depth of soil with good soil moisture status is greater than that of soil with poor soil moisture status. In addition, in the vegetated regions, the luster and color of vegetation with good soil moisture status is better than that of vegetation with poor soil moisture status. Therefore, color segmentation thresholds are separately set for the soil exposed regions and the vegetated regions, so as to segment the regions with good soil moisture status and the regions with poor soil moisture status in the soil exposed regions, and to segment the regions with good soil moisture status and the regions with poor soil moisture status in the vegetated regions.

Images of sub-regions are divided into a plurality of small square grids on the basis of grid method (the number of grids is set according to actual demand, and the more grids are divided, the larger the calculation amount, but the higher the accuracy). The number of grids occupied by the regions with good soil moisture status and the number of grids occupied by the regions with poor soil moisture status in the soil exposed regions, as well as the number of grids occupied by the regions with good soil moisture status and the number of grids occupied by the regions with poor soil moisture status in the vegetated regions are acquired. The color segmentation index is calculated by the following expression:

$$ys_f = \frac{sc_t}{sh_t} + \frac{sc_b}{sh_b}$$

where $ys_f$ represents the color segmentation index, $sh_t$ represents the number of grids occupied by the regions with good soil moisture status in the soil exposed regions, sc, represents the number of grids occupied by the regions with poor soil moisture status in the soil exposed regions, $sh_b$ represents the number of grids occupied by the regions with good soil moisture status in the vegetated regions, and $sc_b$ represents the number of grids occupied by the regions with poor soil moisture status in the vegetated regions. The greater the color segmentation index, the poorer the soil moisture status in the sub-region.

An expression for calculating the humidity coefficient is as follows:

$$sd_x = \sum_{i=1}^{n} e^{a_i * sd_i}$$

where $sd_x$ represents the humidity coefficient, i={1, 2, . . . , n}, n being a positive integer, and representing the number of monitoring points set at different soil depths in the sub-region, $sd_i$ represents soil humidity at an $i_{th}$ monitoring point, and $a_i$ represents a weight of the soil humidity at the $i_{th}$ monitoring point, $a_i$ being greater than 0. A larger humidity coefficient indicates a larger overall soil humidity value of the sub-region after weighting, i.e., a better soil moisture status.

In the prior art, a humidity sensor is usually arranged only at one soil depth to monitor the soil humidity, lacking comprehensive analysis of the soil humidity at different depths, and the accuracy is poor.

An expression for calculating the moisture content float coefficient is as follows:

$$hs_f = \int_{t_x}^{t_y} H(t)dt + \int_{t_i}^{t_j} H(t)dt$$

where H (t) represents real-time moisture content of soil in the sub-region, [$t_x$, $t_y$] represents a period for early-warning of environmental evapotranspiration in the sub-region, and [$t_i$, $t_j$] represents a period for early-warning of groundwater level in the sub-region.

The logic for acquiring the period for early-warning of environmental evapotranspiration in the sub-region is as follows. Environmental evapotranspiration of the sub-region is calculated by means of evaporation dishes, which are field instruments commonly used to monitor environmental evapotranspiration. They are tray-like containers, which are filled with water and placed outdoors to estimate evapotranspiration by measuring the amount of water level dropped over a certain period of time. Evaporometers are automated instruments used for recording environmental evapotranspiration. The higher the evapotranspiration, the faster the moisture content of the soil of the sub-region reduces over a certain period of time, and therefore, a period in which evapotranspiration is greater than an evapotranspiration threshold is the period for early-warning of environmental evapotranspiration in the sub-region.

The logic for acquiring the period for early-warning of groundwater level in the sub-region is as follows. Groundwater level of the sub-region is acquired by means of a radar. Groundwater level has a greater impact on soil moisture status in the sub-region. A higher groundwater level can improve the moisturizing capacity of the soil. Therefore, a period in which the groundwater level is lower than a water level threshold is the period for early-warning of groundwater level in the sub-region, and at this time, the moisturizing capacity of soil decreases, resulting in a poor soil moisture status.

According to positive and negative relationships between the image data and the multi-source data, a moisture status coefficient is calculated by combining the color segmentation index, the humidity coefficient, and the moisture content float coefficient through the following expression:

$$sq_x = \frac{\alpha * sd_x^2 + 1}{\ln\sqrt{\beta * ys_f + \gamma * hs_f}}$$

where $sd_x$ represents the humidity coefficient, $ys_e$ represents the color segmentation index, $hs_f$ represents the moisture content float coefficient, and α, β, and γ represent proportionality coefficients of the humidity coefficient, the color segmentation index, and the moisture content float coefficient, respectively, α, β, and γ being greater than 0.

From the formula for calculating the moisture status coefficient $sq_x$, it can be known that the larger the value of the moisture status coefficient $sq_x$ is, the better the soil moisture status in the sub-region is. Therefore, the value of the moisture status coefficient $sq_x$ obtained by the calculation is compared with a preset moisture status threshold. If the value of the moisture status coefficient $sq_x$ is greater than or equal to the moisture status threshold, it is assessed that the sub-region has a good soil moisture status, and if the value of the moisture status coefficient $sq_x$ is less than the moisture status threshold, it is assessed that the sub-region has a poor soil moisture status.

Overall soil moisture status of the monitoring region is comprehensively analyzed according to the soil moisture status of the various sub-regions.

After the soil moisture status of various sub-regions in the monitoring region is assessed, the overall soil moisture status of the monitoring region is comprehensively analyzed according to the soil moisture status of the various sub-regions, which includes the following steps.

The number of sub-regions is acquired, and values of the moisture status coefficient $sq_x$ of the various sub-regions are acquired.

An average moisture status coefficient value of all the sub-regions is calculated.

A moisture status coefficient dispersion degree of the monitoring region is calculated on the basis of the values of the moisture status coefficient and the average moisture status coefficient value of the sub-regions.

Soil moisture status of the monitoring region and a variation trend of the soil moisture status are analyzed according to the moisture status coefficient dispersion degree of the monitoring region.

An expression for calculating the moisture status coefficient dispersion degree of the monitoring region is as follows:

$$jq_s = \sqrt{\frac{\sum_{b=1}^{c}(R_b - \overline{R})^2}{c-1}}$$

where b={1, 2, 3, . . . , c}, c representing the number of sub-regions, and being a positive integer, $R_b$ represents a value of the moisture status coefficient $sq_x$ in a $b_{th}$ sub-region, and $\overline{R}$ represents the average moisture status coefficient value.

If the average moisture status coefficient value is greater than or equal to the moisture status threshold and the moisture status coefficient dispersion degree is less than or equal to a dispersion threshold, the overall soil moisture status of the monitoring region is analyzed to be good, and trends towards good in the future (i.e., values of the moisture status coefficient $sq_x$ of a plurality of sub-regions in the monitoring region are greater than or equal to the moisture status threshold).

If the average moisture status coefficient value is greater than or equal to the moisture status threshold and the moisture status coefficient dispersion degree is greater than the dispersion threshold, the overall soil moisture status of the monitoring region is analyzed to be moderate, and there are unstable factors in the future development trend of the soil moisture status (i.e., values of the moisture status coefficient $sq_x$ of some sub-regions in the monitoring region are less than the moisture status threshold).

If the average moisture status coefficient value is less than the moisture status threshold and the moisture status coefficient dispersion degree is greater than the dispersion threshold, the overall soil moisture status of the monitoring region is analyzed to be poor, and there are unstable factors in the future development trend of the soil moisture status (i.e., values of the moisture status coefficient $sq_x$ of some sub-regions in the monitoring region are greater than or equal to the moisture status threshold).

If the average moisture status coefficient value is less than the moisture status threshold and the moisture status coefficient dispersion degree is less than or equal to the dispersion threshold, the overall soil moisture status of the monitoring region is analyzed to be very poor, and trends towards bad in the future (i.e., values of the moisture status coefficient $sq_x$ of a plurality of sub-regions in the monitoring region are less than the moisture status threshold).

In the present application, the moisture status coefficient is calculated by combining the color segmentation index, the humidity coefficient and the moisture content float coefficient, bringing about a more comprehensive and accurate analysis. Moreover, after the soil moisture status of a plurality of sub-regions is analyzed, the overall soil moisture status in the monitoring region as well as the development trend of the soil moisture status are determined by the analyzed soil moisture status of the plurality of sub-regions, which is conducive to formulating a management policy by the administrator.

The above formulas are de-dimensionalized and numerical values are taken for calculation. The formulas are closest to real situation by the collection of a large number of data for software simulation. The preset parameters in the formulas are set by the skilled in the art according to actual situation.

The above embodiments may be realized entirely or partially in software, hardware, firmware or a combination thereof. When software is used for realization, the above embodiments may be realized entirely or partially in the form of a computer program product, which includes one or more computer instructions or computer programs. When the computer instructions or the computer programs are loaded on or executed by the computer program product, a process or function according to the embodiments of the present disclosure is generated entirely or partially. The computer may be a general-purpose computer, a special purpose computer, a computer network or other programmable apparatuses. The computer instructions may be stored in a computer-readable storage medium or transmitted from one computer-readable storage medium to another. For example, the computer instructions may be transmitted from one website, computer, server, or data center to another website, computer, server, or data center via a wired or wireless (e.g, infrared, wireless, microwave, etc.) mode. The computer-readable storage medium may be any available medium that the computer can access or a data storage apparatus such as a server, a data center, etc. that contains one or more available media integrated. The available media may be magnetic media (e.g., floppy disk, hard disk, magnetic tape), optical media (e.g., digital video disk (DVD)), or semiconductor media. The semiconductor media may be solid state disks.

It is to be understood that the term "and/or" herein is merely used for describing the association relationship of associated objects, indicating that three types of relationships may exist, for example, A and/or B may represent that the following three conditions: A exists alone, both A and B exist, and B exists alone, and A and B may be singular or plural. In addition, the character "/" herein generally represents that an "or" relationship between the associated objects before and after, but may also represent an "and/or" relationship, and the specific reference may be made to the context.

In the present application, "at least one" means one or more, and "a plurality of" means two or more. "At least one item of the following", or similar expressions, refers to any combination of these items, including any combination of single item or plural items. For example, at least one of a, b, or c, may be represented as: a, b, c, a-b, a-c, b-c, or a-b-c, in which, a, b, c may be singular or plural.

It is to be understood that in various embodiments of the present application, the size of the serial number in above various processes does not imply the order of execution, which is to be determined by function and inherent logic without constituting any limitation on the implementation processes of the embodiments of the present application.

Those of ordinary skill in the art may realize that units and algorithmic steps of the various embodiments described in conjunction with the embodiments disclosed herein are capable of being implemented in electronic hardware, or a combination of computer software and electronic hardware. Whether these functions are performed in hardware or software depends on the specific application and design constraints of the technical solution. Those professional skilled may use different methods for each particular application to implement the described function, but such implementation is not to be considered outside the scope of the present application.

It is clearly understood by those skilled in the art to which they belong that, for the convenience and brevity of the description, the specific working processes of the system, apparatuses, and units described above may be referred to the corresponding processes in the foregoing method of the embodiments, and will not be repeated here.

In the several embodiments provided in the present application, it is to be understood that a system, an apparatus, and a method disclosed, may be realized in other ways. For example, the above-described embodiments of the device are merely schematic; the division of the described unit, which is merely a logical functional division, may be performed in a different way when actually implemented; and a plurality of units or components may be combined or may be integrated into another system, some features may be ignored, or not executed. In addition, mutual coupling, direct coupling, or communication connection shown or discussed may be realized via some interfaces, and indirect coupling or communication connection between apparatuses or units may be electrical, mechanical or otherwise.

The units described as illustrated as separated components may or may not be physically separated, and the components shown as units may or may not be physical units, i.e., they may be located in a single place or may also be distributed to a plurality of network units. Some or all of these units may be selected to realize the objective of the solution of the embodiment according to actual needs.

Furthermore, the various functions in the present application may be integrated in a single processing unit, the individual units may physically exist separately, or two or more units may be integrated in a single unit.

The function may be stored in a computer-readable storage medium if it is realized as a software functional unit and sold or used as a stand-alone product. On the basis of this understanding, the technical solutions of the present application may be embodied essentially or in part as a contribution to the prior art, or part of the technical solution may be embodied in the form of a software product, which is a computer software product stored in a storage medium including a number of instructions for allowing a computer device (which may be a personal computer, a server, or a network device, etc.) to carry out all or part of the steps of the method described in the various embodiments of the present application. The aforementioned storage media include: a U flash disc, a mobile hard disk, a read-only-memory (ROM), a random-access-memory (RAM), a magnetic disk or a compact disc (CD), and other media that can store program code.

The above mentioned are only the specific embodiments of the present application, but the scope of the protection of the present application is not limited to this. Any variations or replacements that can easily be thought of by any skilled familiar with the technical field of the present application within the technical scope disclosed by the present application shall be covered by the scope of the protection of the present application. Therefore, the scope of the protection of the present application is to be defined by the attached claims.

The invention claimed is:

1. An intelligent monitoring method for soil moisture status based on remote sensing technology, comprising the following steps:
    S1: dividing a monitoring region into a plurality of sub-regions by a processing end, acquiring image data of various sub-regions on the basis of remote sensing satellites, acquiring multi-source data related to soil moisture status of the monitoring region on the basis of sensor devices, and pre-processing the image data and the multi-source data,
    S2: comprehensively analyzing the image data and the multi-source data, and assessing soil moisture status of the various sub-regions,
    S3: comprehensively analyzing overall soil moisture status of the monitoring region according to the soil moisture status of the various sub-regions,
    S4: presenting the overall soil moisture status of the monitoring region in a visualization manner, and
    S5: sending a visualization report to an administrator, wherein
    in step S2, the image data and the multi-source data are comprehensively analyzed, the image data comprising a color segmentation index, and the multi-source data comprising a humidity coefficient and a moisture content float coefficient; and
    in step 2, the assessing soil moisture status of the various sub-regions comprises the following steps:
    S2. 1: calculating a moisture status coefficient $sq_x$ by combining the color segmentation index, the humidity coefficient, and the moisture content float coefficient through the following expression:

$$sq_x = \frac{\alpha * sd_x^2 + 1}{\ln\sqrt{\beta * ys_f + \gamma * hs_f}}$$

where $sd_x$ represents the humidity coefficient, $ys_f$ represents the color segmentation index, $hs_f$ represents the moisture content float coefficient, and $\alpha$, $\beta$, and $\gamma$ represent proportionality coefficients of the humidity coefficient, the color segmentation index, and the moisture content float coefficient, respectively, $\alpha$, $\beta$, and $\gamma$ being greater than 0, and
    S2. 2: assessing soil moisture status in a sub-region to be good if a value of the moisture status coefficient $sq_x$ is greater than or equal to a moisture status threshold, and assessing soil moisture status in a sub-region to be poor if a value of the moisture status coefficient $sq_x$ is less than the moisture status threshold; and
    in step S3: the comprehensively analyzing overall soil moisture status of the monitoring region according to the soil moisture status of the various sub-regions comprises the following steps:

S3.1: acquiring the number of sub-regions, and acquiring values of the moisture status coefficient $sq_x$ of the various sub-regions, S3.2: calculating an average moisture status coefficient value of all the sub-regions, S3.3: calculating a moisture status coefficient dispersion degree of the monitoring region on the basis of the values of the moisture status coefficient $sq_x$ and the average moisture status coefficient value of the sub-regions, and S3.4: analyzing soil moisture status of the monitoring region and a variation trend of the soil moisture status according to the moisture status coefficient dispersion degree of the monitoring region, wherein in step S3.4, an expression for calculating the moisture status coefficient dispersion degree $jq_s$ of the monitoring region is as follows:

$$jq_s = \sqrt{\frac{\sum_{b=1}^{c}(R_b - \overline{R})^2}{c-1}}$$

where b={1, 2, 3, . . . , c}, c representing the number of sub-regions, and being a positive integer, $R_b$ represents a value of the moisture status coefficient $sq_x$ in a $b_{th}$ sub-region, and $\overline{R}$ represents the average moisture status coefficient value, if the average moisture status coefficient value is greater than or equal to the moisture status threshold and the moisture status coefficient dispersion degree is less than or equal to a dispersion threshold, the overall soil moisture status of the monitoring region being analyzed to be good, and trending towards good in the future, if the average moisture status coefficient value is greater than or equal to the moisture status threshold and the moisture status coefficient dispersion degree is greater than the dispersion threshold, the overall soil moisture status of the monitoring region being analyzed to be moderate, and unstable factors existing in the future development trend of the soil moisture status, if the average moisture status coefficient value is less than the moisture status threshold and the moisture status coefficient dispersion degree is greater than the dispersion threshold, the overall soil moisture status of the monitoring region being analyzed to be poor, and unstable factors existing in the future development trend of the soil moisture status, and if the average moisture status coefficient value is less than the moisture status threshold and the moisture status coefficient dispersion degree is less than or equal to the dispersion threshold, the overall soil moisture status of the monitoring region being analyzed to be very poor, and trending towards bad in the future.

2. The intelligent monitoring method for soil moisture status based on remote sensing technology according to claim 1, wherein an expression for calculating the color segmentation index is as follows:

$$ys_f = \frac{sc_t}{sh_t} + \frac{sc_b}{sh_b}$$

where $ys_f$ represents the color segmentation index, $sh_t$ represents the number of grids occupied by regions with good soil moisture status in soil exposed regions, $sc_t$ represents the number of grids occupied by regions with poor soil moisture status in the soil exposed regions, $sh_b$ represents the number of grids occupied by regions with good soil moisture status in vegetated regions, and $sc_b$ represents the number of grids occupied by regions with poor soil moisture status in the vegetated regions.

3. The intelligent monitoring method for soil moisture status based on remote sensing technology according to claim 2, wherein an expression for calculating the humidity coefficient is as follows:

$$sd_x = \sum_{i=1}^{n} e^{a_i * sd_i}$$

where $sd_x$ represents the humidity coefficient, i={1, 2, . . . , n}, n being a positive integer, and representing the number of monitoring points set at different soil depths in the sub-region, $sd_i$ represents soil humidity at an $i_{th}$ monitoring point, and $a_i$ represents a weight of the soil humidity at the $i_{th}$ monitoring point, $a_i$ being greater than 0.

4. The intelligent monitoring method for soil moisture status based on remote sensing technology according to claim 3, wherein an expression for calculating the moisture content float coefficient is as follows:

$$hs_f = \int_{t_x}^{t_y} H(t)dt + \int_{t_i}^{t_j} H(t)dt$$

where H(t) represents real-time moisture content of soil in the sub-region, [$t_x$, $t_y$] represents a period for early-warning of environmental evapotranspiration in the sub-region, and [$t_i$, $t_j$] represents a period for early-warning of groundwater level in the sub-region.

5. The intelligent monitoring method for soil moisture status based on remote sensing technology according to claim 4, wherein the logic for acquiring the period for early-warning of environmental evapotranspiration in the sub-region is as follows: calculating environmental evapotranspiration in the sub-region by means of an evaporation dish, a period in which evapotranspiration is greater than an evapotranspiration threshold being the period for early-warning of environmental evapotranspiration in the sub-region.

6. The intelligent monitoring method for soil moisture status based on remote sensing technology according to claim 5, wherein the logic for acquiring the period for early-warning of groundwater level in the sub-region is as follows: acquiring groundwater level of the sub-region by means of a radar, a period in which groundwater level is lower than a water level threshold being the period for early-warning of groundwater level in the sub-region.

* * * * *